US00PP21201P3

(12) United States Plant Patent

Faedi et al.

(10) Patent No.: US PP21,201 P3

(45) Date of Patent: Aug. 17, 2010

(54) STRAWBERRY PLANT NAMED 'RECORD'

(50) Latin Name: ***Fragaria×ananassa* Duch**
Varietal Denomination: Cv. Record

(75) Inventors: Walther Faedi, Forli (IT); Gianluca Baruzzi, Forli (IT); Michele Baudino, Cuneo (IT); Roberto Giordano, Cuneo (IT); Pierluigi Lucchi, Diegaro di Cesena (IT)

(73) Assignee: C.R.P.V., Diegaro di Cesena (IT)

( * ) Notice: Subject to any disclaimer, the term of this patent is extended or adjusted under 35 U.S.C. 154(b) by 141 days.

(21) Appl. No.: 11/819,056

(22) Filed: Jun. 25, 2007

(65) Prior Publication Data

US 2009/0038039 P1 Feb. 5, 2009

(51) Int. Cl.
*A01H 5/00* (2006.01)

(52) U.S. Cl. ..... Plt./208

(58) Field of Classification Search ..... Plt./208
See application file for complete search history.

(56) References Cited

U.S. PATENT DOCUMENTS

PP10,982 P * 6/1999 D'Ercole et al. ..... Plt./208

OTHER PUBLICATIONS

UPOV ROM GTITM Computer Database, GTI Jouve Retrieval Software 2008/02 Citation for 'Record'.*

Fadei, W. et al. New varieties and emerging selections for strawberry production in nothern Italy. Rivista di Frutticoltura e di Ortofloricoltura vol. 68 (4): p. 12-16, 18 and 20-21 Apr. 2006.*

Bablefish web translation available at bablefish.yahoo.com.*

Baruzzi et al. "Sugar Lia and Record, two new cultivars" Informatore Agrario vol. 62(26) pp. 39-42 Jun. 23, 2006.*

* cited by examiner

*Primary Examiner*—Wendy C. Haas

(74) *Attorney, Agent, or Firm*—Buchanan Ingersoll & Rooney PC

(57) ABSTRACT

A new and distinct *Fragaria×ananasa* Duch. plant is provided that is the product of a controlled breeding program that was carried out in Italy. Non-remontant bearing late in the season is exhibited. The new Strawberry plant abundantly forms attractive fruit that commonly is larger in size than that of the 'Idea' cultivar (U.S. Plant Pat. No. 10,982). Also, when compared to the 'Idea' cultivar, the new cultivar displays a more erect growth habit, is commonly more vigorous and more productive, forms larger flowers that commonly are borne in a more upright position, forms smaller achenes that are positioned below the fruit surface, and commonly forms longer fruiting trusts. The new cultivar is particularly well suited for the summer planting of cold storage frigo plants.

4 Drawing Sheets

Botanical/commercial classification: *Fragaria×ananassa* Duch/Strawberry Plant.

Varietal denomination: Cv. Record.

SUMMARY OF THE INVENTION

The new Strawberry cultivar was created by artificial pollination performed in 1992 in Italy wherein two parents were crossed which previously had been studied in the hope that they would contribute the desired characteristics. The female parent (i.e., the seed parent) of the new cultivar was the 'Idea' cultivar (U.S. Plant Pat. No. 10,982), and the male parent (i.e., the pollen parent) was the 'Marmolda' cultivar (non-patented in the United States). The parentage of the new cultivar can be summarized as follows:

'Idea'×'Marmolda'.

The seeds resulting from the above pollination were sown and small plants were obtained which were physically and biologically different from each other.

The new cultivar first fruited during 1994 at the CRA-Istituto Sperimentale per la Frutticoltura, Sezione di Forli - Po Valley, Italy. Selective study resulted in the identification of a single plant of the new cultivar.

It was found that the new Strawberry cultivar of the present invention possesses the following combination of characteristics:

(a) generally displays a more erect growth habit than the 'Idea' cultivar (U.S. Plant Pat. No. 10,982), and commonly is more vigorous and more productive, (b) forms larger flowers than the 'Idea' cultivar that commonly are borne in a more upright position, (c) forms attractive fruit that commonly is larger in size than that of the 'Idea' cultivar, (d) forms generally smaller achenes than the 'Idea' cultivar which commonly are positioned below the fruit surface, and (e) commonly forms longer fruiting trusts than the 'Idea' cultivar.

The new plant of the present invention is an attractive June bearing Strawberry cultivar that is well suited for commercial fruit production. The new cultivar is particularly well suited for the summer planting of cold storage frigo plants, and has perfoinied well in organic culture and in non-fumigated soil. The production pattern of the new cultivar is similar to that of the 'Idea' cultivar.

The new cultivar initially was designated 92, 340, 3, and subsequently has been named 'Record'.

BRIEF DESCRIPTION OF THE PHOTOGRAPHS

The accompanying photographs show as nearly true as it is reasonably possible to make the same in color illustrations of this character typical specimens of the new cultivar. The plants were being grown in the field using commercial fruit growing conditions at Diegaro di Cesena, Italy.

DETAILED DESCRIPTION

Figure 1:
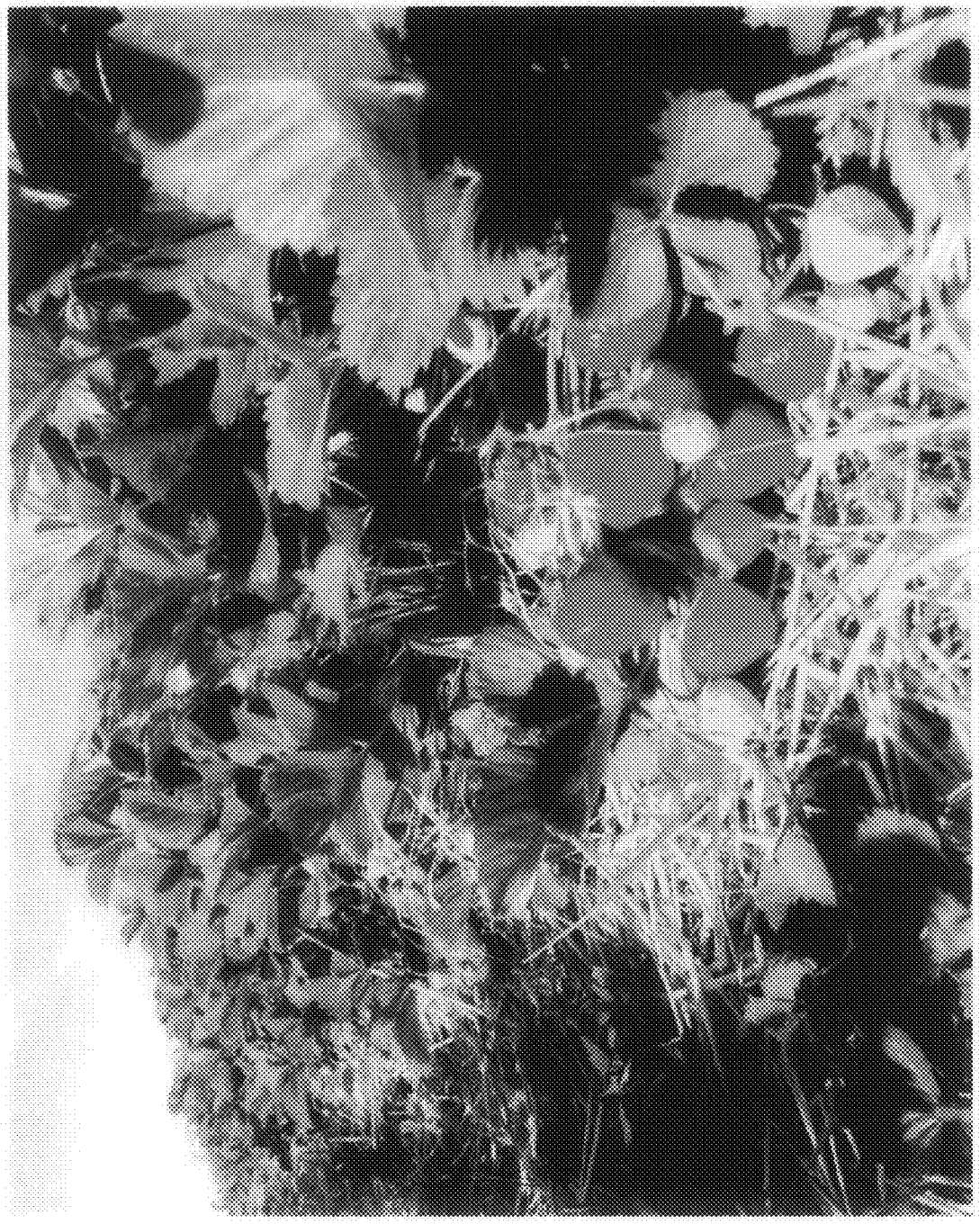
FIG. 1 depicts the general growth habit and the fruiting characteristics of the new cultivar. Typical strawberries are shown in various stages of maturity.
Figure 2:
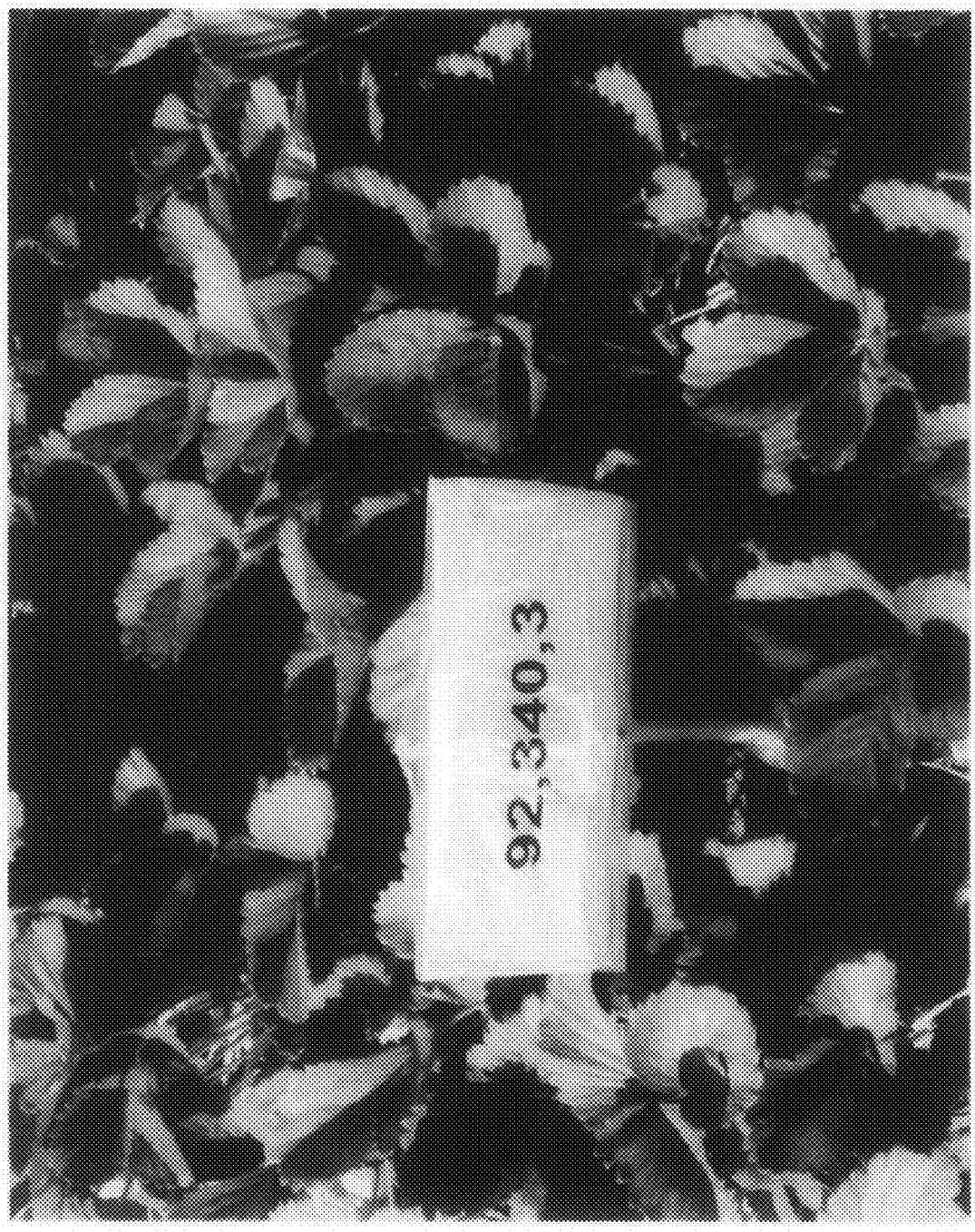
FIG. 2 depicts the typical foliage of the new cultivar.

The description is based on the observation of typical plants of the new cultivar under field growing conditions at Diegaro di Cesena, Italy. The new cultivar was selected and evaluated on soil which possessed a pH of 7.6, and consisted of approximately 39 percent clay, approximately 24 percent sand, and approximately 37 percent silt. The plant performed with good adaptability to these pedological conditions without evidencing any specific symptoms of abiotic stress.

Plant:

*Growth habit.*—Intermediate and more upright than the generally prostrate growth habit of the 'Idea' cultivar.

*Crown number.*—Very high, commonly approximately 3.5 on average, and similar to that of the 'Idea' cultivar.

*Density.*—Dense and similar to that of the 'Idea' cultivar.

*Vigor.*—Strong, generally greater than the medium-strong vigor of the 'Idea' cultivar, the most growth commonly is displayed in May, and commonly approximates 20 cm during a growing season to yield a plant that reaches approximately 40 cm.

*Uniformity of vigor.*—Medium high and commonly greater than the medium uniformity of the 'Idea' cultivar.

*Productivity.*—Very high and commonly greater than that of the 'Idea' cultivar.

Foliage:

*Shape of terminal leaflet.*—Elliptical-rounded and similar to that of the 'Idea' cultivar.

*Margin.*—Crenate and similar to that of the 'Idea' cultivar.

*Size.*—Medium large which can be compared to the medium size of the 'Idea' cultivar. A typical leaf length commonly is approximately 7.3 cm±0.4 cm, and a typical leaf width commonly is approximately 7.4 cm±0.4 cm.

*Color.*—The upper (adaxial) surface commonly is near Green Group 135A, and the under (abaxial) surface commonly is near Green Group 137C when evaluated while using The R.H.S. Colour Chart of The Royal Horticulture Society, London, England.

*Glossiness.*—Slight on upper surface and commonly less than that of the 'Idea' cultivar.

Flowering:

*Time.*—Later, and commonly slightly later than that of the 'Idea' cultivar. A typical blooming period is approximately April 22nd to May 10th.

*Position.*—Commonly approximately level with the canopy. This can be compared with a position generally beneath the canopy for the 'Idea' cultivar.

*Petal color.*—White, and commonly near White Group 155D.

*Petal number.*—Commonly 5 to 8.

*Petal shape.*—Elliptical which can be compared to a more rounded configuration for the 'Idea' cultivar. The petals commonly are approximately 8 mm±2 mm in width.

*Petal texture.*—Smooth on both surfaces.

*Corolla size.*—Relatively large and approximately the same size of the calyx which can be compared to a medium size for the 'Idea' cultivar. A typical bloom diameter commonly is approximately 3.1 cm±0.2 cm.

*Stamens.*—Present.

*Reblooming capacity.*—None.

Fruit:

*Bearing type.*—Not remontant.

*Size.*—For a typical fruit commonly approximately 5.1 cm±0.3 cm in length and approximately 4.5 cm±0.3 cm in width.

*Weight.*—Very large and generally greater than that of the 'Idea' cultivar as described in greater detail hereafter. The typical average weight of a primary fruit is approximately 42 g on average. The typical weight of subsequent fruit commonly is approximately 26 g on average. As indicated hereafter an average berry weight of 29.0 g was observed throughout a single harvest.

*Shape.*—Generally conical and somewhat regular and uniform with a rounded tip. This can be compared to a more globose-conic configuration for the 'Idea' cultivar.

*Insertion of calyx.*—Generally level.

*Skin resistance.*—Medium.

*External color.*—More red which can be compared to more orange-red coloration of the 'Idea' cultivar as described in greater detail hereafter. Such external fruit color of the new variety commonly is near Red Group N30A when evaluated while using the R.H.S. Colour Chart of The Royal Horticultural Society, London, England.

*Internal color.*—The internal fruit color commonly is near Red Group 38A when evaluated while using the R.H.S. Colour Chart of The Royal Horticultural Society, London, England.

Figure 3:
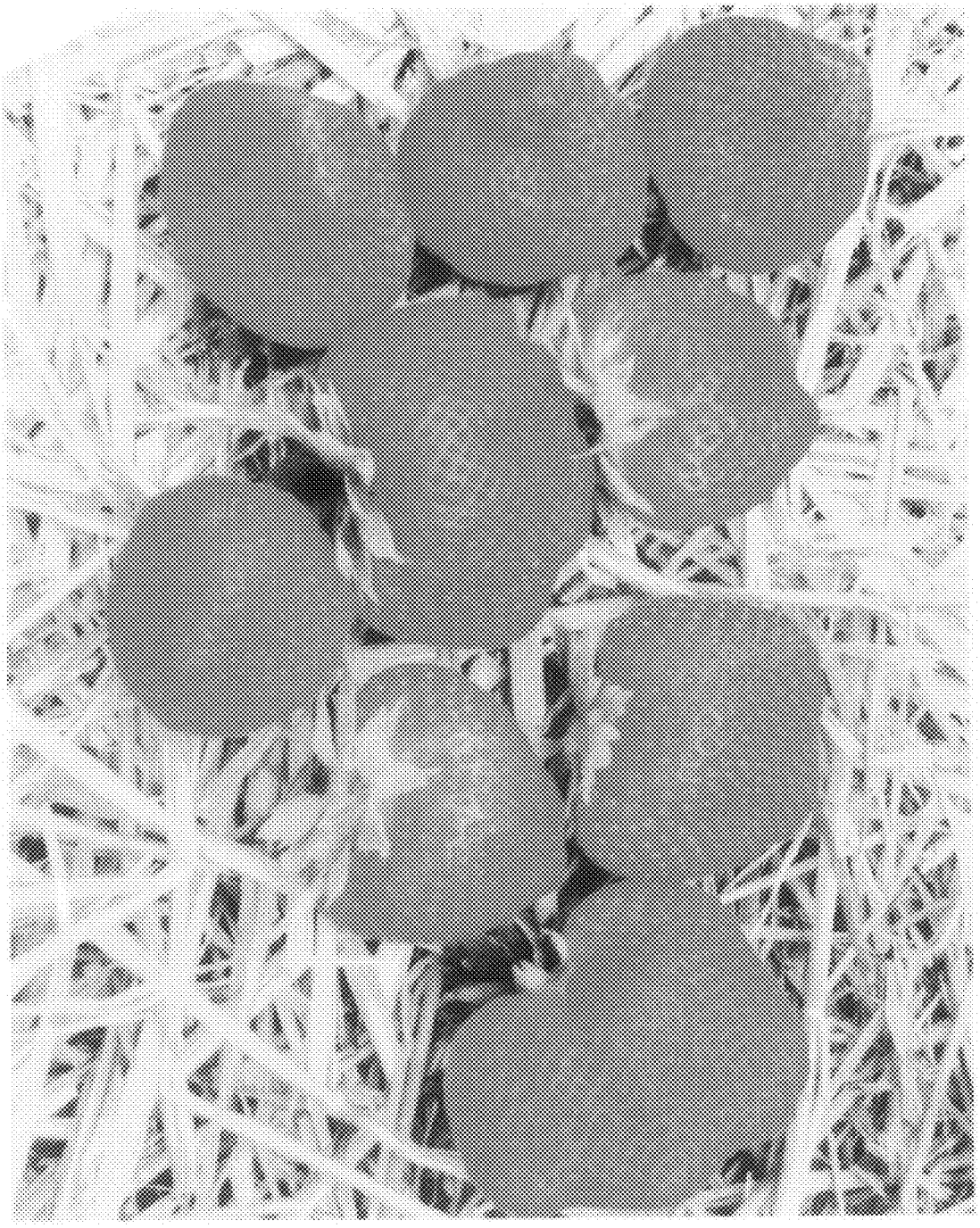
FIG. 3 depicts typical attractive mid-season fruit of the new cultivar.

*Glossiness.*—Very strong as shown in FIG. 3.

*Homogeneity of color.*—Medium.

*Tip color.*—Same as the remainder of fruit.

*Calyx shape.*—Rounded.

*Calyx size.*—Medium, commonly approximately 2.7 to 2.9 cm.

*Calyx color.*—Commonly near Green Group 136A on the upper (internal) surface and near Green Group 137C on under (external) surface.

*Removal of calyx.*—Medium easy and slightly less difficult than for the 'Idea' cultivar.

*Sepals.*—Commonly approximately 10 to 12 in number, elongated, medium in size, commonly approximately 0.9 to 1.0 cm, possess an entire margin, and are detached.

*Achenes.*—Relatively small, commonly yellow-red in coloration, present in a medium to high frequency and inserted below the fruit surface. The achenes of the 'Idea' cultivar tend to be more yellow in coloration, larger in size, slightly fewer in number, and commonly are present at the same level as the fruit surface.

*Flesh.*—Pale pink in coloration, medium in firmness, possesses a small internal cavity, and possesses medium sweetness. The flesh of the 'Idea' cultivar tends to be more orange-red in coloration as indicated in greater detail hereafter, commonly possesses a larger internal cavity, and commonly is of greater sweetness.

*Acidity.*—Medium as described in greater detail hereafter and generally less than that of the 'Idea' cultivar.

*Firmness.*—When evaluated with a Chatillon-type penetrometer utilizing a plug of 6 mm diameter, a flesh firmness value of approximately 324 g on average has been observed.

*Harvest time.*—Late and approximately the same as that of the 'Idea' cultivar. A typical harvest period is approximately May 21st to June 11th.

Disease tolerance: The new cultivar during observations to date has been tolerant to *Colletotrichum acutatum, Sphaerotheca macularis* and soil-borne pathogens. Some susceptibility to *Diplocarpon earliana* and *Xanthomonas fragariae* has been exhibited.

Representative CIELAB color comparisons of the leaves (adaxial and abaxial), external fruit coloration, and internal fruit coloration for the new 'Record' cultivar and the 'Idea' cultivar are set forth below. The color determinations expressed hereafter were made in accordance with Minolta Chroma Meter II Reflectance while utilizing an 8 mm window and represent average values upon the evaluation of 20 leaves and 20 fruit.

| Leaf Color | | | | | | |
|---|---|---|---|---|---|---|
| Adaxial | | 'Record' | | | 'Idea' | |
| L* | | | | | | |
| mean | | 38.6 | | | 38.2 | |
| range | 34.9 | — | 41.2 | 34.4 | | 41.5 |
| a* | | | | | | |
| mean | | −14.1 | | | −15.2 | |
| range | −16.3 | — | −10.5 | −17.8 | | −12.8 |
| b* | | | | | | |
| mean | | 18.1 | | | 19.9 | |
| range | 11.9 | — | 21.8 | 15.4 | | 24.8 |
| L* | | | | | | |
| mean | | 53.6 | | | 52.0 | |
| range | 51.3 | — | 56.3 | 48.7 | | 54.3 |
| a* | | | | | | |
| mean | | 13.3 | | | −13.7 | |
| range | −15.5 | — | −11.5 | −14.8 | | −12.6 |
| b* | | | | | | |
| mean | | 17.6 | | | 19.0 | |
| range | 15.1 | — | 22.0 | 14.3 | | 21.9 |

| Fruit Color (External) | | | | | | |
|---|---|---|---|---|---|---|
| | | 'Record' | | | 'Idea' | |
| L* | | | | | | |
| mean | | 41.1 | | | 45.3 | |
| range | 35.8 | — | 46.0 | 39.0 | | 49.8 |

-continued

| Fruit Color (External) | | | | | | |
|---|---|---|---|---|---|---|
| | | 'Record' | | | 'Idea' | |
| a* | | | | | | |
| mean | | 36.6 | | | 36.8 | |
| range | 31.6 | — | 39.0 | 33.1 | | 40.8 |
| b* | | | | | | |
| mean | | 28.0 | | | 31.6 | |
| range | 21.7 | — | 34.3 | 23.6 | | 36.3 |

| Fruit Color (Internal) | | | | | | |
|---|---|---|---|---|---|---|
| | | 'Record' | | | 'Idea' | |
| L* | | | | | | |
| mean | | 66.5 | | | 57.0 | |
| range | 51.3 | — | 75.7 | 44.9 | | 64.3 |
| a* | | | | | | |
| mean | | 13.1 | | | 29.1 | |
| range | 1.1 | — | 32.9 | 16.3 | | 37.6 |
| b* | | | | | | |
| mean | | 21.3 | | | 31.0 | |
| range | 11.4 | — | 34.9 | 21.8 | | 39.4 |

During the 2003 to 2005 growing seasons the yields of the new 'Record' cultivar were compared with those of the 'Idea' cultivar. The results are reported hereafter.

| | Yield, g/Plant | | Average | Earli- | Flesh |
|---|---|---|---|---|---|
| Cultivar | Commer-cial | Total | Fruit Weight, g | ness Index | Firmness, g |
| 'Record' | 1,049 | 1,176 | 29.0 | 156 | 270 |
| 'Idea' | 986 | 1,107 | 24.7 | 155 | 290 |

It will be observed that the 'Record' cultivar produced larger fruit in greater yields. The 'Record' cultivar initiates and finishes production at about the same time as the 'Idea' cultivar, but tends to form larger quantities of fruit in the second half of the harvest period. Accordingly, the Earliness Index for 'Record' cultivar is slightly later. The fruit fiirmness for the 'Record' cultivar is substantially similar to that of the 'Idea' cultivar for all practical purposes.

Chemical analysis of the fruit yielded the following average results:

| | Sugar Content g/100 g | | | Acid Content, mg/100 g | | | Soluble Solids | Titratable Acid |
|---|---|---|---|---|---|---|---|---|
| Culti-var | fruc-tose | glu-cose | su-crose | mal-aic | cit-ric | as-corbic | Content, °Brix | meq/ 100 g |
| 'Re-cord' | 2.6 | 2.4 | 1.1 | 302 | 658 | 55 | 6.9 | 9.9 |
| 'Idea' | 2.8 | 2.6 | 1.5 | 246 | 732 | 57 | 7.1 | 10.9 |

The lesser content of sucrose and citric acid in the fruit of the 'Record' cultivar commonly yields a somewhat lesser favor intensity than that of the 'Idea' cultivar.

Figure 4:
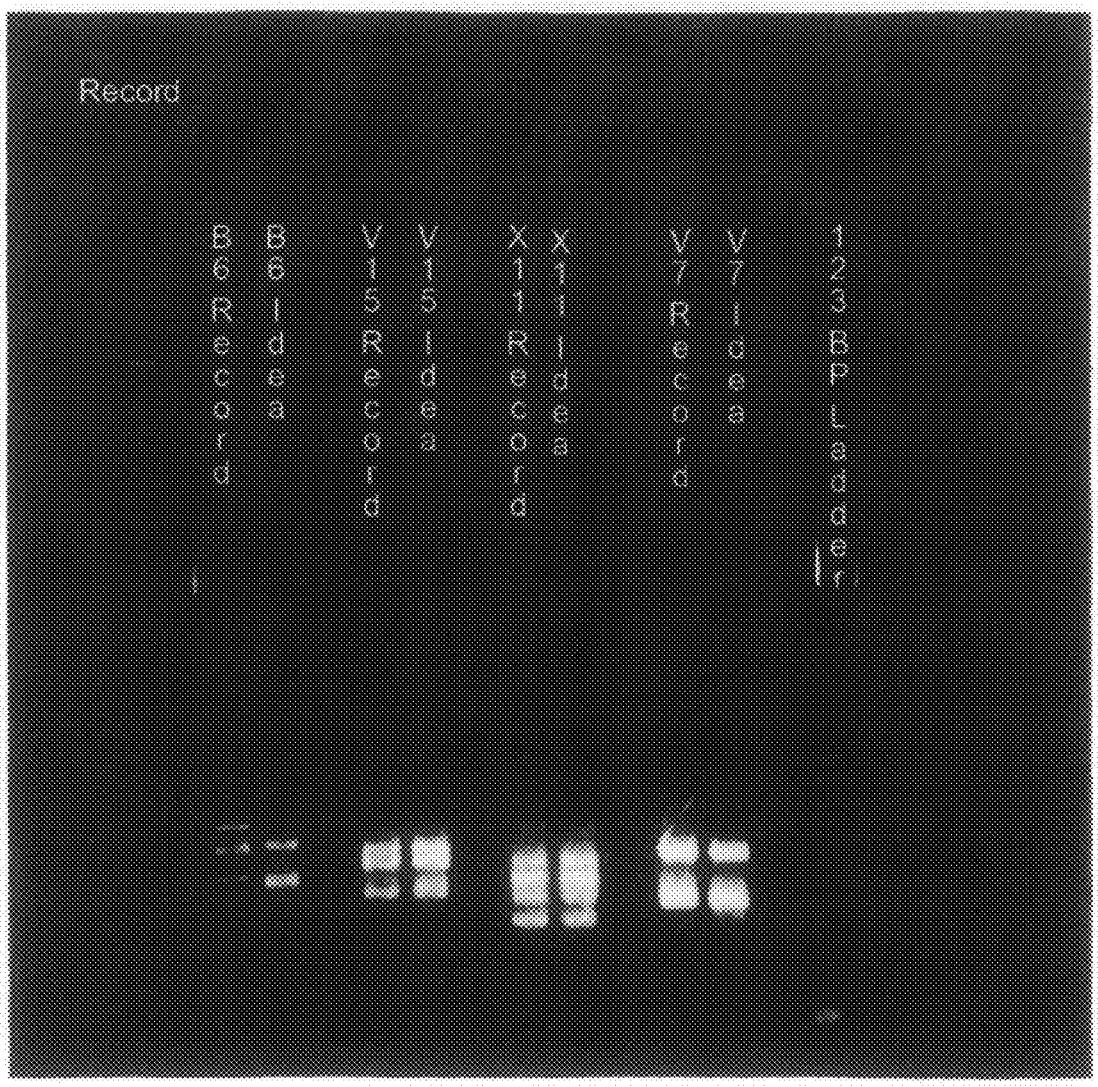
FIG. 4 depicts a comparison of the new cultivar of the present invention and the 'Idea' cultivar through the use of RAPD (Randomly Amplified Polymorphic DNA markers) as described in greater detail hereafter.

As indicated in FIG. 4, genetic fingerprinting of leaf extracts of the 'Record' and 'Idea' cultivars was carried out using RAPD (Randomly Amplified Polymorphic DNA markers). This analysis was carried out at The University of Minnesota, Minneapolis, Minn., U.S.A., at the laboratory of Dr. Jim Luby. The following four standard primers were used:

| | |
|---|---|
| B6 | (5'-TGCTCTGCC-3) (SEQ ID NO: 1), |
| V15 | (5'-CAGTGCCGGT-3') (SEQ ID NO: 2), |
| X11 | (5'-GGAGCCTCAG-3') (SEQ ID NO: 3), and |
| V7 | (5'-GAAGCCAGCC-3') (SEQ ID NO: 4). |

A standard DNA molecular marker (i.e., a 123BP ladder) is included. The banding patterns for the 'Record' cultivar using primers B6 and V15 are shown to distinct from the banding patterns of the 'Idea' cultivar.

Plants of the new 'Record' cultivar have not been observed under all possible environmental conditions to date. Accordingly, it is possible that the phenotypic expression may vary somewhat with changes in light intensity and duration, cultural practices, and other environmental conditions.

SEQUENCE LISTING

```
<160> NUMBER OF SEQ ID NOS: 4

<210> SEQ ID NO 1
<211> LENGTH: 9
<212> TYPE: DNA
<213> ORGANISM: Artificial
<220> FEATURE:
<223> OTHER INFORMATION: Standard Primer

<400> SEQUENCE: 1

tgctctgcc                                                          9


<210> SEQ ID NO 2
<211> LENGTH: 10
<212> TYPE: DNA
<213> ORGANISM: Artificial
<220> FEATURE:
<223> OTHER INFORMATION: Standard Primer

<400> SEQUENCE: 2

cagtgccggt                                                        10


<210> SEQ ID NO 3
<211> LENGTH: 10
<212> TYPE: DNA
<213> ORGANISM: Artificial
<220> FEATURE:
<223> OTHER INFORMATION: Standard Primer

<400> SEQUENCE: 3

ggagcctcag                                                        10


<210> SEQ ID NO 4
<211> LENGTH: 10
<212> TYPE: DNA
<213> ORGANISM: Artificial
<220> FEATURE:
<223> OTHER INFORMATION: Standard Primer

<400> SEQUENCE: 4

gaagccagcc                                                        10
```

We claim:

1. A new and distinct Strawberry plant having the following combination of characteristics:

(a) generally displays a more erect growth habit than the 'Idea' cultivar (U.S. Plant Pat. No. 10,982), and commonly is more vigorous and more productive, (b) forms larger flowers than the 'Idea' cultivar that commonly are borne in a more upright position, (c) forms attractive fruit that commonly is larger in size than that of the 'Idea' cultivar, (d) forms generally smaller achenes than the 'Idea' cultivar which commonly are positioned below the fruit surface, and (e) commonly forms longer fruiting trusts than the 'Idea' cultivar;

substantially as illustrated and described.

* * * * *